Figure 1:
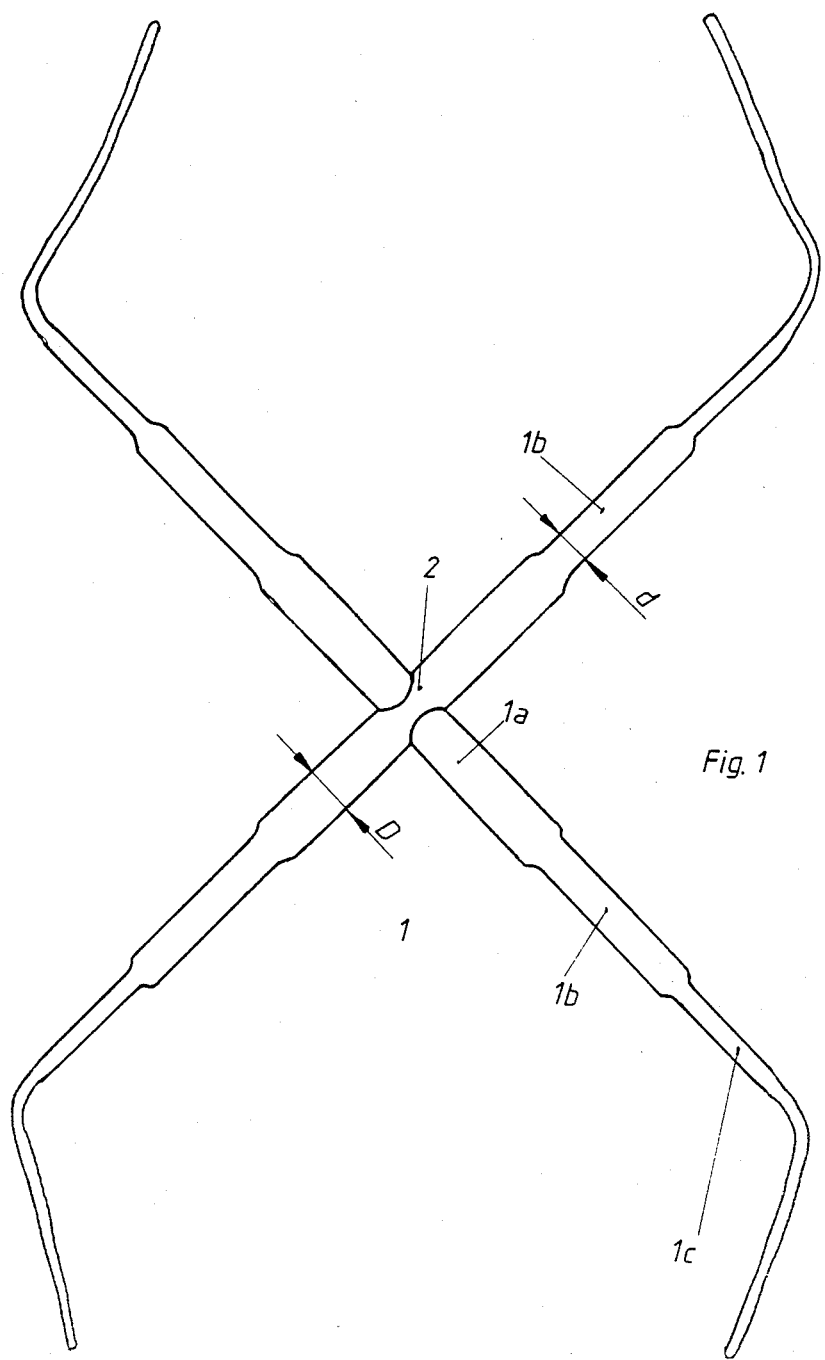

United States Patent [19]
Mansat

[11] Patent Number: 4,863,471
[45] Date of Patent: Sep. 5, 1989

[54] CRUCIAL LIGAMENT REPLACEMENT FOR A KNEE JOINT

[75] Inventor: Christian Mansat, Balma, France

[73] Assignees: Sulzer Brothers Limited, Winterthur; Protek AG, Berne, both of Switzerland

[21] Appl. No.: 131,127

[22] Filed: Dec. 10, 1987

[30] Foreign Application Priority Data

Jan. 7, 1987 [CH] Switzerland ................ 29/87

[51] Int. Cl.$^4$ .............................................. A61F 2/08
[52] U.S. Cl. ....................................................... 623/13
[58] Field of Search ................... 623/16, 18, 13, 11, 623/12; 272/126

[56] References Cited

U.S. PATENT DOCUMENTS

| | | | |
|---|---|---|---|
| 3,896,500 | 7/1975 | Rambert | 623/13 |
| 4,047,714 | 9/1977 | Powell | 272/126 |
| 4,728,329 | 3/1988 | Mansat | 623/13 |

FOREIGN PATENT DOCUMENTS

| | | | |
|---|---|---|---|
| 2717924 | 10/1978 | Fed. Rep. of Germany | 128/DIG. 25 |
| 0820809 | 4/1981 | U.S.S.R. | 623/13 |

Primary Examiner—Richard J. Apley
Assistant Examiner—David J. Isabella
Attorney, Agent, or Firm—Kenyon & Kenyon

[57] ABSTRACT

The crucial ligament replacement is formed with two cords to define the anterior crucial ligament and posterior crucial ligament. The cords interpenetrate each other within sections of relatively great flexibility and relatively large longitudinal stretchability so that mutual movement between the two cords at the crossing point is reduced to a minimum where an attrition are greatly reduced at the crossing point.

8 Claims, 3 Drawing Sheets

CRUCIAL LIGAMENT REPLACEMENT FOR A KNEE JOINT

This invention relates to a crucial ligament replacement for a knee joint.

As is known, various types of artificial ligaments have been constructed for different parts of the body. For example, U.S. Pat. No. 728,329 describes an artificial ligament replacement which is constructed of a cord having a plurality of concentric textile tubes as well as sections of different longitudinal stretchability. If such an artificial ligament is used as a crucial ligament replacement in a knee joint and, if both natural crucial ligaments are replaced simultaneously, it has been customary to insert one of these known constructions as the anterior and a second as the posterior crucial ligament separately and "lying side by side". However, it has been found in practice that these two artificial crucial ligaments undergo relatively heavy attrition and wear during their relative movement, which cannot be tolerated.

Accordingly, it is an object of the invention to reduce as much as possible friction and attrition in an artificial crucial ligament replacement for cases where the anterior and posterior crucial ligaments are replaced by a prosthesis simultaneously.

Briefly, the invention provides a crucial ligament replacement for a knee joint comprising a first cord defining an anterior crucial ligament and a second cord defining a posterior crucial ligament interpenetrating with the first cord.

Each cord is formed of a plurality of concentric textile tubes with at one section of relatively large longitudinal stretchability and relatively great flexibility. In addition, the cords are interpenetrated with each other in the sections of relatively large longitudinal stretchability. To this end in the simplest case, one cord is pulled, for example by means of an awl-like instrument, through the flexible region of the other cord.

When in place, the relatively movement between the interpenetrated cords and, hence also the friction and attrition, is greatly reduced. This is because the ligaments expand, primarily due to their great longitudinal stretchability before they begin to "slide" on one another.

If two different artificial ligaments are used to replace and anterior and a posterior crucial ligament, four points are required for fixation on the bones. If, however, the cords for the anterior and posterior crucial ligaments consist of one and the same band, with a loop between the two cords, the number of anchorage points on the bones can be reduced to one or two.

Figure 2:
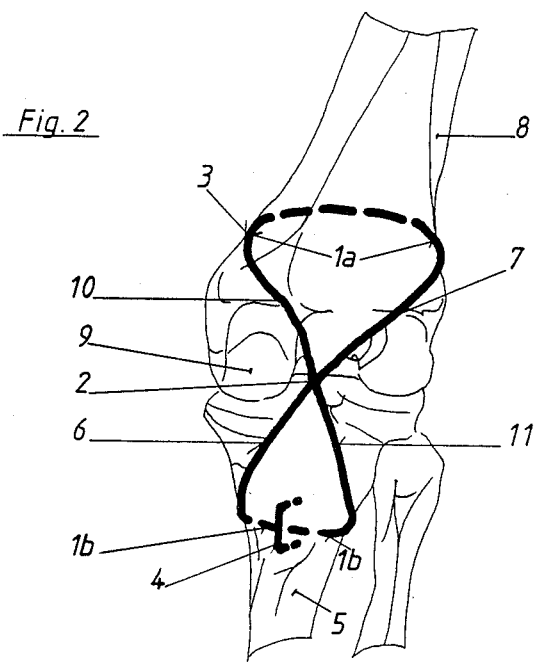
Figure 3:
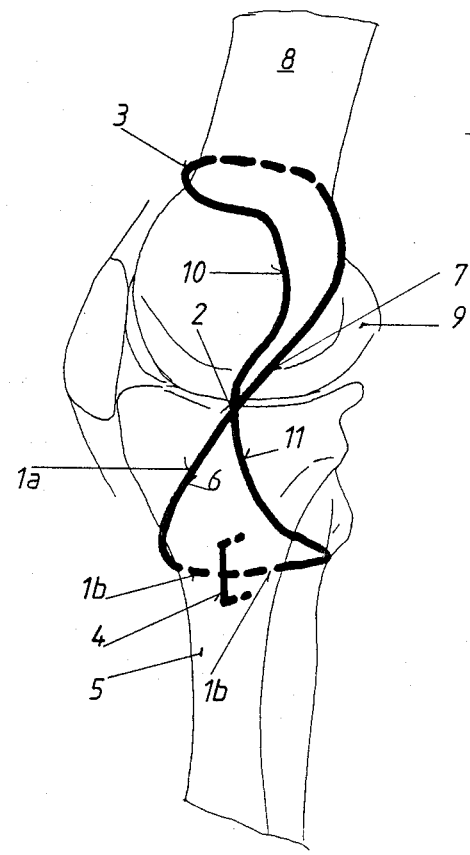

These and other objects and advantages of the invention will become more apparent from the following detailed description taken in conjunction with the accompany drawings wherein:

FIG. 1 illustrates a crucial ligament replacement formed of two cords in accordance with the invention;

FIG. 2 schematically illustrates a posterior view of a knee joint having a crucial ligament replacement made of a single band with two cords; and FIG. 3 illustrates a view of FIG. 2 from the left, viewed from the medial side.

Referring to FIG. 1, the crucial ligament replacement is constructed for use in a knee joint. As indicated, the crucial ligament replacement is formed of two cords 1 defining an anterior crucial ligament and a posterior crucial ligament. Each cord 1 is formed of a plurality of concentric textile tubes, as is known, with a central section or region 1a having relatively large longitudinal stretchability and relative great flexibility. As indicated each central section 1a is of an enlarged diameter D. In addition, each cord has a region 1b of relatively low flexibility adjacent the central section 1a on each side. As indicated, the regions of low flexibility has a smaller diameter d.

In the illustrated embodiment, the diameter of the flexible central region 1a is approximately 12 millimeters while the more rigid sections 1b have a diameter of 7 millimeters. Further, the replacement is shown in approximately natural size. Each cord 1 is formed without a core and may consist of braided tubes, the braid angles of which are different in the regions of different flexibility relative to the axial direction. However, the braid angle would be the same for all tubes within a given region. Besides braiding, other methods for the working of the threads may be used, such as weaving, knitting and the like which permit a minimum value for the elastic longitudinal stretchability of the respective cords 1.

The tubes from which the cords are made may be of multi-filament or monofilament threads. Further, the threads may be made of natural fibers such as silk, or may be made of synthetic fibers, such as polyester, polyethylene or known resorbable materials. For the production of a cord 1, a plurality of concentric tubes or plies, for example, 20 to 30 are "layered" one over the other.

For the production of braided tubes, twisted threads of a plurality, for example, 60 monofilaments consisting for example of polyester and having a diameter of 0.01 to 0.03 millimeters have proved especially satisfactory. As illustrated, each cord is provided with a thin threading section 1c at each end. In this respect, the thin section 1c may be formed by a few of the tubes or only the outermost tube. In addition, the thin sections 1c may be stiffened or reinforced by a lining of insert or by impregnation in a hardening compound.

The different longitudinal stretchability and the different flexibility characteristics of the individual regions 1a, 1b are obtained, in the construction of a cord 1 of braided tubes, by different braiding angles relative to the cord axis. The flexibility will be greater, the flatter the braiding the angle is inclined against the cord axis.

As indicated in FIG. 1, the two cords 1 interpenetrate in the flexible region 1a at a crossing point 2. A simple method of producing an artificial ligament replacing both crucial ligaments consists in pulling one of the two cords 1 through the central region 1a of the other cord 1, for example with the aid of an awl. The high flexibility of the braid in the flexible region 1a fixes the cords 1 mutually at the crossing point 2 thereby largely preventing a "sliding" and rubbing of the cords 1 against each other.

Referring to FIG. 2, the crucial ligament replacement may be made on one piece. In this case, a loop 3 is located between and connects the cords 1 to each other. In this case, the interpenetration of the cords occurs during an implantation procedure.

In order to implant the ligament replacement, a staple 4 is used to anchor a flexible region 1b to the tibia 5. The cord 1 is then passed through a bore 6 in the tibia from the lower left to the upper right in order to form a replacement of one of the crucial ligaments. The cord is then passed through a femoral bone passage 7 to the lateral exterior side of the femur 8 and looped around the femur 8 above the condyle 9 interiorly on the outside and thence through a second bore 10 in the femur 8. The cord then passes between the femur 8 and the tibia 5 to form the second crucial ligament with the crossing point 2 being formed, as described above. The band is then passed through a further passage 11 in the tibia 5 with a partial looping of the tibia 5 back to the staple 4. The two ends of the band are then anchored jointly by the staple 4.

Of note, it is possible to also fix each end region 1b with a separate staple or by another known technique. Also, one of the femur passages 7 or 10 can be eliminated by passing the cord along the bone surface between the condyle 9 on its way toward the loop 3.

The invention thus provides a crucial ligament replacement for a knee joint which avoids any significant attrition and wear between the anterior and posterior crucial ligaments.

Further, the invention substantially eliminates sliding and rubbing of the two cords forming the anterior and posterior crucial ligaments on each other so that wear and attrition are greatly reduced.

Figure 4:
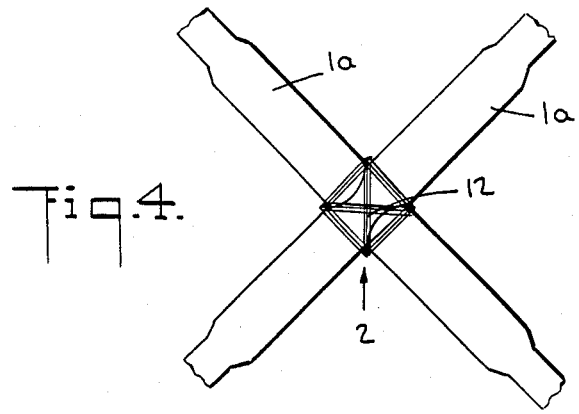
Figure 5:
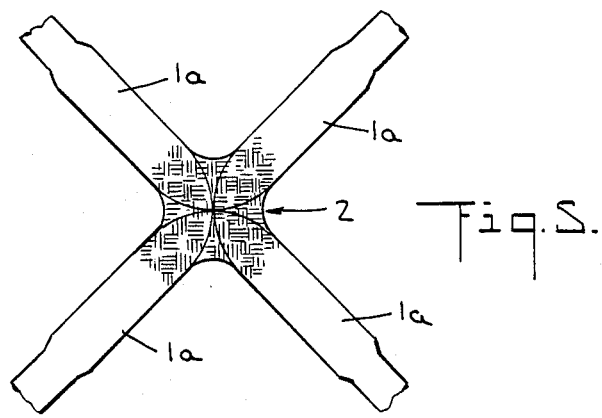
Figure 6:
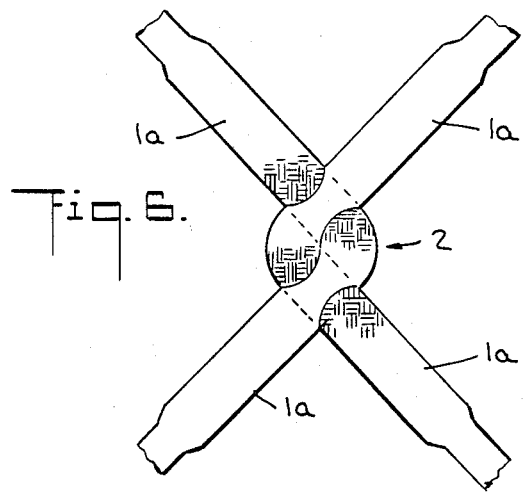

FIGS. 4 to 6 show further possibilities of an interpenetration of the two cords 1 at a crossing point 2.

The interpenetration according to FIG. 4 is the same as in FIG. 1 but additionally the location of the crossing point 2 is secured against shifting by single threads which are wound about the crossing point 2 crosswise.

In FIG. 5 at the crossing point 2 the threads of each braided tube running to the point branch into the three other branches and are interlaced with a third of the threads coming from the other cords.

In FIG. 6 each of the cords is pulled through the other for a double interpenetration which is a safety device against shifting of the crossing point 2. That is, one cord interpenetrates the second cord at a first point while the second cord interpenetrates the first cord at a second point spaced from the first point to secure the cords against shifting.

What is claimed is:

1. A crucial ligament replacement for a knee joint comprising a first cord defining an anterior crucial ligament and formed of a plurality of concentric textile tubes with at least one section of relatively large longitudinal stretchability and relatively great flexibility; and a second cord defining a posterior crucial ligament and formed of a plurality of concentric textile tubes with at least one section of relatively large longitudinal stretchability and relatively high flexibility interpenetrating said section of said first cord.

2. A crucial ligament replacement as set forth in claim 1 which further comprises a loop between and connecting said cords.

3. A crucial ligament replacement as set forth in claim wherein each cord has a region of relatively low flexibility adjacent said section of high flexibility thereof.

4. A crucial ligament replacement as set forth in claim 3 wherein said region of each cord is of less diameter than said section thereof.

5. A crucial ligament for a knee joint comprising a first cord defining an anterior crucial ligament;

a second cord defining a posterior crucial ligament interpenetrating said first cord at a crossing point; and single threads wound about said cords at said crossing point to secure said cords against shifting thereat.

6. A crucial ligament replacement as set forth in claim 5 wherein each cord has a flexible central region, and an adjacent section of lower flexibility on each side of said central region.

7. A crucial ligament replacement for a knee joint comprising a first cord of concentric tubes of braided threads defining an anterior crucial ligament; and a second cord of concentric tubes of braided threads defining a posterior crucial ligament and crossing said first cord at a crossing point to define four branches, said threads of at least one tube branching from one of said branches into the remaining three branches to secure said cords against shifting at said crossing point.

8. A crucial ligament replacement for a knee joint comprising first cord of concentric tubes defining an anterior crucial ligament;

a second cord of concentric tubes defining a posterior crucial ligament crossing said first cord, said second cord interpenetrating said first cord at a first point and said first cord interpenetrating said second cord at a second point spaced from said first point to secure said cords against shifting.

* * * * *

UNITED STATES PATENT AND TRADEMARK OFFICE
CERTIFICATE OF CORRECTION

PATENT NO. : 4,863,471

DATED : Sept. 5, 1989

INVENTOR(S) : CHRISTIAN MANSAT

It is certified that error appears in the above-identified patent and that said Letters Patent is hereby corrected as shown below:

```
Column 1, line 34 "at one" should be -at least one-
Column 1, line 48 "and" should be -an-
Column 1, line 56, 57 "accompany" should be -accompanying-
Column 2, line 4 "relative" should be -relatively-
Column 2, line 8 "has" should be -have-
Column 2, line 30 "30 are" should be -30, are-
Column 2, line 33 ", 60" should be -, of 60-
Column 2, line 40 "of" should be -or-
Column 4, line 11 "claim" should be -claim 1-
```

Signed and Sealed this

Ninth Day of October, 1990

Attest:

HARRY F. MANBECK, JR.

*Attesting Officer*  *Commissioner of Patents and Trademarks*